United States Patent [19]

Croix et al.

[11] 3,962,460

[45] June 8, 1976

[54] ETHER COMPOUNDS AS INHALANT ANESTHETICS

[75] Inventors: Louise S. Croix, Summit; Alex J. Szur, North Plainfield, both of N.J.

[73] Assignee: Airco, Inc., Montvale, N.J.

[22] Filed: Aug. 20, 1974

[21] Appl. No.: 498,975

Related U.S. Application Data

[63] Continuation-in-part of Ser. No. 295,640, Oct. 6, 1972, abandoned.

[52] U.S. Cl. ............................ 424/342; 260/614
[51] Int. Cl.² ...................................... A61K 31/08
[58] Field of Search ............... 424/342 ; 260/614 F

[56] References Cited
OTHER PUBLICATIONS

Terrell et al., J. of Med. Chemistry, vol. 15, No. 6, 1972, pp. 606–608.
Chemical Abstracts, 73:24909m (1970).

*Primary Examiner*—Jerome D. Goldberg
*Attorney, Agent, or Firm*—Roger M. Rathbun; Edmund W. Bopp; H. Hume Mathews

[57] ABSTRACT

Aliphatic ether compounds having a formula selected from the group consisting of

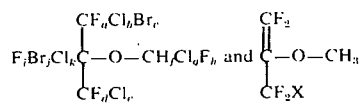

wherein each of $a$ and $d$ is 2 or 3; each of $b$, $c$, $e$, $i$, $j$ and $k$ is 0 or 1; each of $f$ and $g$ is 0, 1, 2, or 3; $h$ is 0, 1, or 2; $a + b + = 3$; $d + e = 3$; $f + g + h = 3$; $i + j + k = 1$; and X is F or Cl; with the provisos that when $a$ and $d$ are both 3, then $i$ is 1, $f$ is 0, 1, or 2, and $g$ is 0, 1, or 3; when $g$ is 2, then $f$ is 1; when $c$ is 1, then f is 3 and $k$ is 0; when $j$ is 1, then $c$ is 1; and when both $b$ and $e$ are 1, then $i$ is 1, are useful as solvents and dispersants for fluorinated materials. In addition, the compounds methyl 1-bromo-1,1,2,3,3,3-hexafluoroisopropyl ether and methyl 1,2-dichloro-1,1,3,3,3-pentafluoroisopropyl ether are useful as inhalation anesthetics.

6 Claims, No Drawings

ETHER COMPOUNDS AS INHALANT ANESTHETICS

This is a continuation-in-part application of application Ser. No. 295,640 filed Oct. 6, 1972, now abandoned.

This invention relates to aliphatic ether compounds having a formula selected from the group consisting of

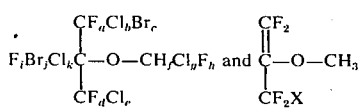

wherein each of $a$ and $d$ is 2 or 3; each of $b, c, e, i, j,$ and $k$ is 0 or 1; each of $f$ and $g$ is 0, 1, 2, or 3; $h$ is 0, 1, or 2; $a + b + c = 3$; $d + e = 3$; $f + g + h = 3$; $i + j + k = 1$; and X is F or Cl; with the provisos that when $a$ and $d$ are both 3, then $i$ is 1, $f$ is 0, 1, or 2, and $g$ is 0, 1, or 3; when $g$ is 2, then $f$ is 1; when $c$ is 1, then $f$ is 3 and $k$ is 0; when $j$ is 1, then $c$ is 1; and when both $b$ and $e$ are 1, then $i$ is 1.

The ether compounds of this invention are easily miscible with other organic liquids, including fats and oils, and have useful solvent properties, for example as solvents for fluorinated olefins and other fluorinated materials, such as fluoro waxes. The compounds of this invention may be used to prepare pastes and dispersions of such materials useful for coatings and the like, and may be used as degreasing agents. In the latter capacity, for example, the ether compounds of this invention can be used as solvents to remove grease or other oily substances from metal surfaces that are to be painted.

In addition, the compounds of the formula selected from the group consisting of

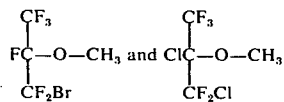

lend themselves to effective use as inhalant anesthetics in respirable mixtures containing life-supporting concentrations of oxygen, with or without other inhalation anesthetics, such as nitrous oxide. Administration of these compounds may be by any of the well known techniques for administering general inhalation anesthetics, for example by using the open drop, semiclosed, or closed systems.

The effective amount of the anesthetics of this invention to be employed depends on the level of anesthesia to which the mammal is to be brought, the rate at which anesthesia is to be induced, and the length of time over which anesthesia is to be maintained. The amount used should be sufficient to provide a significant anesthetic effect, but not so much as to produce unacceptable deleterious side effects. Vapor concentrations at which the anesthetic compounds of this invention may often be used are about 1 to 6 volume percent, with the concentration actually employed depending on the choice of anesthetic; for instance, methyl 1-bromo-1,1,2,3,3,3-hexafluoroisopropyl ether may often be used in an amount of about 4 to 6%, and methyl 1,2-dichloro-1,1,3,3,3-pentafluoroisopropyl ether may often be used in an amount of about 1 to 3%.

The amount of anesthesia to be used can be regulated, starting with a small amount of the ether and gradually increasing the amount until the desired plane of anesthesia is reached. By then monitoring the physical reactions of the mammal, as is the usual procedure, the duration and plane of anesthesia can be readily controlled.

The following examples illustrate the preparation of the compounds of the present invention.

EXAMPLE I

This example illustrates the preparation of heptafluoroisopropyl methyl ether, used in other examples herein to prepare the compounds of the present invention.

A 1 gal., glass lined, stirred autoclave was charged with 203 g. of potassium fluoride and 1000 ml. of acetonitrile and sealed. Commercially obtained hexafluoroacetone, 830 g., was added as a liquid under pressure during a 2 hour period, followed by 440 g. of dimethyl sulfate in 1 hour. The stirred autoclave was heated at 90°C. for 16 hours. The cooled contents were distilled through a 75 in. × 1 in. metal packed column with a dry ice condenser to yield 588 g. of product (b.p. 28°–30°C., 98.3% pure). Washing with water removed the contaminating acetonitrile and produced a sample 99.8% pure. The structure was confirmed by composition analysis and infrared spectroscopy.

EXAMPLE II

This example illustrates the preparation of chloromethyl heptafluoroisopropyl ether and trichloromethyl heptafluoroisopropyl ether.

A 500 ml. water jacketed glass flask, connected to a dry-ice condenser whose exit was attached to a water scrubber, was charged with 777 g. of heptafluoroisopropyl methyl ether. While maintaining the temperature at 25°C. with water cooling and while irradiating with an incandescent bulb, gaseous chlorine was introduced at such a rate as to be completely consumed. The effluent, gaseous HCl was caught in the scrubber and titrated to follow the course of the reaction. When 2 moles of chlorine per mole of ether had been consumed, the reaction was stopped. The liquid, 354 g., contained the following mixture by analysis:

```
 7.1 wt. %  (CF_3)_2CF—O—CH_2Cl
87.8 wt. %  (CF_3)_2CF—O—CHCl_2
 4.0 wt. %  (CF_3)_2CF—O—CCl_3
 1.1 wt. %  acetonitrile
```

Fractionation at atmospheric pressure yielded a large forecut, 228 g., b.p. 63°–72°C., of mixed mono and dichloro ethers, an 87 g. middle cut, b.p. 72°C., of $(CF_3)_2CF - O - CHCl_2$, 99.9% pure, and a 27 g. residue containing 49.1% of the trichloro ether, $(CF_3)_2F - O - CCl_3$. Redistillation of the forecut and purification by gas chromatography gave $(CF_3)_2CF - O - CH_2Cl$, b.p. 63°C., of 99.9% purity. Composition and infrared analyses confirmed the structures.

EXAMPLE III

This example illustrates the preparation of chlorofluoromethyl heptafluoroisopropyl ether.

In an all copper apparatus, dried and purged with $N_2$, was placed 107 g. of $(CF_3)_2CF - O - CHCl_2$ and 4 g. of $SbCl_5$. While stirring and cooling at 0°C., gaseous HF was metered in and continued until the generation at HCl ceased. The water washed liquid was distilled to give 31 g., b.p. 45°–46°C., of $(CF_3)_2CF - O - CHFCl$ of 99.2% purity.

EXAMPLE IV

This example illustrates the preparation of chlorofluoromethyl heptafluoroisopropyl ether and difluoromethyl heptafluoroisopropyl ether.

When a mixture of 93 g. of $(CF_3)_2CF - O - CHCl_2$ and 10 g. of $SbCl_5$ was treated with HF as above, the 17 g. of product contained 40.0 % of $(CF_3)_2CF - O - CHFCl$ and 50.0% of $(CF_3)_2CF - O - CHF_2$.

EXAMPLE V

This example illustrates the preparation of fluoromethyl heptafluoroisopropyl ether.

In an all copper apparatus, dried and purged with $N_2$, was placed 142 g. of $(CF_3)_2CF - O - CH_2Cl$ and 10 g. of $SbCl_5$. While stirring and cooling at 0°C., gaseous HF was admitted until the generated HCl ceased. The water washed liquid product was distilled to give 16 g. b.p. 38°–40°C., of $(CF_3)_2CF - O - CH_2F$, of 96% purity.

EXAMPLE VI

This example illustrates the preparation of methyl 1-chlorohexafluoroisopropyl ether.

By the method described in Example I, above, a mixture of 35.4 g. of potassium fluoride and 180 g. of acetonitrile in an autoclave was treated with 152 ml. of chloropentafluoroacetone and then with 75.5 g. of dimethyl sulfate. The autoclave was stirred and heated at 90°C. for 24 hours. The cooled contents were distilled to yield 103 g. of product, bp. 59°–60°C., which contained a mixture of 80 wt. % $CF_2Cl(CF_3CF - O - CH_3$ and 20 wt. % acetonitrile. Water washing removed the solvent and subsequent distillation gave pure $CF_2Cl(CF_3)CF - O - CH_3$, b.p. 63°C., $n_D^{20}$ 1.3064, 99.9% purity.

EXAMPLE VII

This example illustrates the preparation of 1-chlorohexafluoroisopropyl chloromethyl ether.

Using the method described in Example II, above, 173 g. of $CF_2Cl(CF_3)CF - O - CH_3$ from Example VI was photochlorinated at 30°–40°C. until 0.8 mole of HCl was evolved. The crude product showed the presence of 93.5% of the monochloromethyl ether. Purification by gas chromatography gave $CF_2Cl(CF_3)CF - O - CH_2Cl$, bp. 94°C., of 99.9% purity. Structure was confirmed by composition analysis and infrared.

EXAMPLE VIII

This example illustrates the preparation of 1-chlorohexafluoroisopropyl dichloromethyl ether.

Using the method described in Example II, 462 g. of $CF_2Cl(CF_3)CF - O - CH_3$ was photochlorinated at 50°–70°C. until 4.24 moles of HCl was evolved. The water washed product, 557 g., was distilled under vacuum to give a center fraction, b.p. 62.5°C./180 mm. Hg., $n_D^{20}$ 1.3535, of $CF_2Cl(CF_3)CF - O - CHCl_2$, of 90.5% purity. Structure was confirmed by composition analysis and infrared.

EXAMPLE IX

This example illustrates the preparation of 1-chlorohexafluoroisopropyl trichloromethyl ether.

By the method described in Example II, 287 g. of $CF_2CL(CF_3)cf - O - CHCl_2$ was photochlorinated at 60°C. Chlorine uptake was very slow, and in 20 hours only 0.68 mole of HCl was evolved. The crude product by analysis showed 51.24 wt. % trichloromethyl ether, which was separated by gas chromatography to give $CF_2Cl(CF_3)CF - O - CCl_3$, b.p. 128.5°C., $n_D^{20}$ 1.3774, 99.8% pure. The structure was confirmed by composition analysis and infrared.

EXAMPLE X

This example illustrates the preparation of chlorofluoromethyl 1-chlorohexafluoroisopropyl ether.

In an all copper apparatus, using the method described in Example III, a mixture of 100 g. of $CF_2Cl(CF_3)CF - O - CHCl_2$ from Example VIII and 1.5 g. of $SbCl_5$ was treated with HF for 10 minutes when 0.3 mole of HCl was evolved. The washed liquid was distilled to give 41 g. of $CF_2Cl(CF_3)CF - O - CHFCl$, b.p. 78°C., $n_D^{20}$ 1.3177, 99.7% pure.

EXAMPLE XI

This example illustrates the preparation of difluoromethyl 1-chlorohexafluoroisopropyl ether.

When a mixture of 127 g. of $CF_2Cl(CF_3)CF - O - CHCl_2$ and 5 g. of $SbCl_5$ was fluorinated in the same manner as in Example X, 0.84 mole of HCl was evolved. The washed product was distilled to give 72 g. of $CF_2Cl(CF_3)CF - O - CHF_2$, b.p. 51.8°C., $n_D^{20}$ 1.2829 of 99.8% purity.

EXAMPLE XII

This example illustrates the preparation of pentafluoroisopropenyl methyl ether.

A mixture of 118 g. of KOH, 156 mole of water, and 60 ml. of "Cellosolve" in a reaction flask under a Vigreux column was stirred and heated to 70°C. To the flask, then, 20.3 g. of $CF_2Cl(CF_3)CH - O - CH_3$ (prepared as described in U.S. Pat. No. 3,476,860 of Croix and Szur) was added slowly over a 3 hour period, collecting 90 g. of a low boiling distillate, boiling range 30°–38°C. Careful fractionation gave a center cut, 43 g. of $CF_2=C(CF_3) - O - CH_3$, b.p. 32°C., $n_D^{20}$ 1.2900, 99.9% pure. Structure was confirmed by composition analysis and infrared.

EXAMPLE XIII

Example illustrates the preparation of 1,2-dibromopentafluoroisopropyl methyl ether.

To 46 g. of $CF_2=C(CF_3) - O - CH_3$ prepared as in Example XII, above, was added 16 ml. of liquid bromine. Reaction occurred only under the influence of an incandescent lamp. When all the bromine was absorbed, the liquid product, 71 g., was washed with a solution of sodium bisulfite followed by a solution of potassium carbonate. Vacuum distillation yielded 55 g. (b.p. 57.5°C./53 mm. Hg, or 129°C.) $n_D^{20}$ 1.4055, of $CF_2Br(CF_3)CBr - O - CH_3$ of 99.9% purity.

EXAMPLE XIV

This example illustrates the preparation of 1-bromohexafluoroisopropyl methyl ether.

In a 200 ml. flask a mixture of 210 g. of $CF_2Br(CF_3)CBr - O - CH_3$ from Example XIII, above, 117 g. of anhydrous antimony trifluoride and 17.5 g. of $SbCl_5$ (7.5% by weight of the ether) was stirred and heated under a reflux condenser for 3 hours. The temperature dropped from 130°C. to 105°C. The liquid product was decanted from the salts, washed with 6N HCl solution and distilled to give 53 g. of $CF_2Br(CF_3)CF - O - CH_3$, b.p. 80°C., $n_D^{20}$ 1.3303, 99.9% purity. Structure was confirmed by elemental analysis and infrared.

EXAMPLE XV

This example illustrates the preparation of 1,2-dichloropentafluoroisopropyl methyl ether and 1,2-dichloropentafluoroisopropyl chloromethyl ether.

Into 95 g. of $CF_2=C(CF_3) - O - CH_3$ from Example XII, above, while cooling at −50°C., chlorine was bubbled at such a rate under the activation of incandescent light that it was completely absorbed. The crude product, 137 g., was washed with dilute potassium carbonate and distilled twice to give 54 g. of $CF_2Cl(CF_3)CCl - O - CH_3$, b.p. 96°C., $n_D^{20}$ 1.3520, 99.9% pure.

From the residue of the first distillation was distilled 18 g. of a trichloro product, b.p. 125°C., $n_D^{20}$ 1.3773, 99.3%, which was presumably $CF_2Cl(CF_3(CCl - O - CH_2Cl$.

EXAMPLE XVI

This example illustrates the preparation of 1,2-dichloropentafluoroisopropyl dichloromethyl ether.

When a similar chlorination to that described in Example XV, above, was carried out, first at 0°C., under the influence of light for the absorption of 1 mole of $Cl_2$ and then allowed to rise in temperature to 80°C. during the absorption of 2 more moles of $Cl_2$, a tetrachloro ether was formed. Vacuum distillation of the product gave 259 g., b.p. 64°C./54 mm., Hg, $n_D^{20}$ 1.3874, 97.9% pure, of $CF_2Cl(CF_3)CCl - O - CHCl_2$.

EXAMPLE XVII

This example illustrates the preparation of methyl 1-chlorohexafluoroisopropyl ether.

A mixture of 127 g. of $CF_2Cl(CF_3)CCl - O - CH_3$ (made in Example XV, above), 107 g. of antimony trifluoride, and 9.5 g. of antimony pentachloride was stirred and heated at reflux for 3 hours during which time the temperature dropped from 80°C. to 70°C. The liquid was decanted from the salts, washed with dilute HCl and distilled to give 61 g. of $CF_2Cl(CF_3)CF - O - CH_3$, b.p. 63°C., $n_D^{20}$ 1.3056, 99.9% pure, identical with the methyl ether derived from chloropentafluoroacetone in Example V, above.

EXAMPLE XVIII

This example illustrates the preparation of difluoromethyl 1,2-dichloropentafluoroisopropyl ether.

A mixture of 124 g. of $CF_2Cl(CF_3)CCl - O - CHCl_2$ (made in Example XV, above), 88 g. of antimony trifluoride, and 9.3 g. of antimony pentachloride was stirred and heated at reflux for 3 hours. The liquid product was decanted from the salts, washed with dilute HCl and distilled to give 80 g. of $CF_2Cl(CF_3)CCl - O - CHF_2$, b.p. 84°C., $n_D^{20}$ 1.3247, 99.6% purity. The structure was confirmed by elemental analysis, infrared and NMR.

EXAMPLE XIX

This example illustrates the preparation of 1,3-dichloropentafluoroisopropyl methyl ether.

By the method described in Example I, above, a mixture of 35 g. of potassium fluoride and 180 cc. of acetonitrile in a 1 liter autoclave was treated with 164 g. of commercially obtained dichlorotetrafluoroacetone and then with 76 g. of dimethyl sulfate. The autoclave was stirred and heated at 90°C. for 24 hours. The cooled contents were distilled to yield 110 g., b.p. 73°–76°C., of a mixture containing 37 wt. % of the methyl ether and 59 wt. % of acetonitrile. Several water washes removed the acetonitrile and vacuum distillation of the remaining material yielded 28 g. of $(CF_2Cl)_2CF - O - CH_3$, b.p. 70°C./320 mm. Hg, $n_D^{20}$ 1.3472, 99.9% pure.

EXAMPLE XX

This example illustrates the preparation of dichloromethyl 1,3-dichloropentafluoroisopropyl ether and trichloromethyl 1,3-dichloropentafluoroisopropyl ether.

By the procedure described in Example II, 350 g. of $(CF_2Cl)_2CF - O - CH_3$ was photochlorinated at 50°–70°C. until 2.9 moles of HCl was evolved. Vacuum distillation of the product yielded 355 g. of $(CF_2Cl)_2CF - O - CHCl_2$, b.p. 58°C./40 mm. Hg, $n_D^{20}$ 1.3873, 99.9% pure. The structure was confirmed by elemental analysis and infrared. The 20 g. residue from the vacuum distillation contained 64.8 wt. % of a material presumed to be the trichloromethyl ether, $(CF_2Cl)_2CF - O - CCl_3$.

EXAMPLE XXI

This examaple illustrates the preparation of difluoromethyl 1,3-dichloropentafluoroisopropyl ether and chlorofluoromethyl 1,3-dichloropentafluoroisopropyl ether.

In the copper apparatus described in Example V, above, a mixture of 172 g. of $(CF_2Cl)_2CF - O - CHCl_2$ (made in Example XX, above), and 8.6 g. of $SbCl_5$ were treated with HF at 0°C. until 1.0 mole of HCl was evolved. The water washed product, 143 g., was vacuum distilled to yield 106 g. of $(CF_2Cl)_2CF - O - CHF_2$, b.p. 46°C./200 mm. Hg, $n_D^{20}$ 1.3220, 99.9% pure. Elemental analysis and infrared confirmed the structure.

Gas chromotagraphic analysis of the 17.5 g. residue showed 78 wt. % of a material presumed to be the monoflorination product, $(CF_2Cl)_2CF - O - CHFCl$.

EXAMPLE XXII

This example illustrates the preparation of methyl 3-chlorotetrafluoroisopropenyl ether.

By the same procedures as described in Example XII, above, 165 g. of $(CF_2Cl)_2CH - O - CH_3$ (prepared as described in U.S. Pat. No. 3,476,860 of Croix and Szur) were added slowly to a mixture of 97 g. of KOH, 150 ml. of water and 75 ml. of DIGLYME (diethylene glycol dimethyl ether), collecting 74 g. of crude distillate. After washing with dilute NaOH, redistillation gave 32 g. of $CF_2=C(CF_2Cl) - O - CH_3$, b.p. 65°C., $n_D^{20}$ 1.3424, 99.2% pure. Elemental analysis confirmed the structure.

EXAMPLE XXIII

This example illustrates the preparation of methyl 1,2-bromo-3-chlorotetrafluoroisopropyl ether and methyl 1-bromo-3-chloropentafluoroisopropyl ether.

Addition of 99 g. of bromine according to the method of Example XIII, above, to 110 g. of $CF_2=C(CF_2Cl) - O - CH_3$ (made in Example XXII above) gave a crude dibromo product. After washing and vacuum distilling, 169 g. of $CF_2Br (CF_2Cl)CBR - O - CH_3$, b.p. 62°–66°C./18 mm. Hg, was obtained, 95% pure.

Without further purification, the dibromo compound was fluorinated (by the method described in Example XIV, above) with 89 g. of antimony trifluoride and 12.7 g. of antimony pentafluoride. The liquid product was washed with dilute HCl and dilute aqueous solution of $K_2CO_3$ and distilled to yield 60 g. of $CF_2Br(CF_2Cl)CF-O-CH_2$, b.p. 114°C., $n_D^{20}$ 1.3714, 99.3% pure.

In order to determine the potency of the anesthetic ethers of the present invention as inhalation anesthetics in combination with oxygen, tests were carried out on mice. Each compound tested was at least 99.5% pure as determined by vapor phase chromatography. In the tests, the ether compound is administered to test mice by a standard procedure in which a measured quantity of the agent is placed in a laboratory jar and allowed to completely vaporize so as to give a calculated vapor concentration. The test mice are then quickly placed in the jar and observed. Anesthesia is determined by observing the righting reflex of the mice. Recovery time is measured beginning when the mice are transferred from the test jar to room air and ending when the mice are observed to be able to walk.

In such tests, the methyl 1,2-dichloropentafluoroisopropyl ether induced a very light anesthesia in 4 out of 5 animals in an average time of 8.6 minutes when used at a vapor concentration of 1.25 volume percent. Maintenance was accompanied with some nose scratching and irritation. Recovery required 0.61 minute. At a concentration of 2.5% a deep anesthesia was induced in 2.35 minutes, recovery therefrom requiring 1.15 minutes. There were twitching movements and gasping respiration towards the end of the period in the jar. Good relaxation and analgesia were evident. This compound is nonflammable and has an ethereal odor.

Using a 5.0 volume % vapor concentration of methyl 1-bromohexafluoroisopropyl ether, deep anesthesia, accompanied by analgesia, twisting, jumping and opisthotonus, was induced in 2.0 minutes. Recovery therefrom required 1.5 minutes. This compound is nonflammable and has a slightly ethereal odor.

Since volatile general anesthetics today are generally administered in a closed system involving recycling the exhaled gases for conservation of the relatively expensive agents and protection of operating room personnel, it is required that commercially useful volatile anesthetics intrinsically have good soda-lime stability as do the compounds of the present invention. For example, $CF_3(CF_2Cl)CCl-O-CH_3$ was subjected to soda-lime for a period of about 18 hours to determine its soda-lime stability. The soda-lime was analyzed before and after the test for fluoride ion content and for chloride ion content. About zero parts per million of fluorine and about zero parts per million of chlorine were found to be present before the test. After the test only about 130 parts per million of fluorine and only about 60 parts per million of chlorine were found, establishing that the tested compound exhibited negligible fluoride ion and chloride ion losses and excellent soda-lime stability. Likewise another compound of the present invention, $CF_3(CF_2Cl)CF-O-CH_3$, was similarly tested and after 20 hours of exposure to soda-lime contained about zero parts per million of fluorine and about 487 parts per million of chlorine, also exhibiting excellent soda-lime stability. $CF_3(CF_2Cl)CF-O-CH_2F$ was tested in the same manner. After 20 hours of exposure to soda-lime, the compound contained only 595 parts per million of fluorine and 332 parts per million of chlorine. These results establish excellent soda-lime stability of the compounds of this invention and may be compared to commercial standards. For example, "Halothane" (a commercial anesthetic, formula $CF_3CHClBr$) exhibits 895 parts per million of fluorine and 575 parts per million of chlorine when similarly subjected to soda-lime for 20 hours.

While there has been described what are at present considered to be preferred embodiments of the invention, it will be understood that various modifications may be made therein which are within the true spirit and scope of the invention.

It is claimed:

1. An inhalant anesthetic composition comprising an anesthetically-effective amount of an aliphatic ether compound of a formula selected from the group consisting of

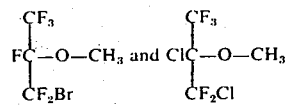

and oxygen.

2. The composition of claim 1 wherein the ether compound is of the formula

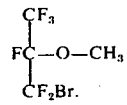

3. The composition of claim 1 wherein the ether compound is of the formula

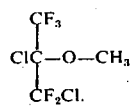

4. A method of anesthetizing an anesthetic-susceptible mammal which comprises administering to the mammal an anesthetically effective amount of aliphatic ether compound of a formula selected from the group consisting of

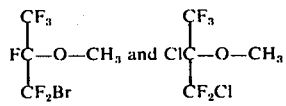

as an inhalation anesthetic while administering life-supporting amounts of oxygen.

5. The method of claim 4 wherein the ether compound is of the formula

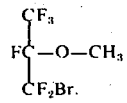

6. The method of claim 4 wherein the ether compound is of the formula

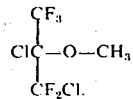

* * * * *